(12) United States Patent
Rydberg et al.

(10) Patent No.: US 10,007,337 B2
(45) Date of Patent: Jun. 26, 2018

(54) EYE GAZE IMAGING

(71) Applicant: SMART EYE AB, Göteborg (SE)

(72) Inventors: Martin Rydberg, Göteborg (SE);
Martin Krantz, Västra Frölunda (SE)

(73) Assignee: Smart Eye AB, Gothenburg (SE)

( * ) Notice: Subject to any disclaimer, the term of this patent is extended or adjusted under 35 U.S.C. 154(b) by 234 days.

(21) Appl. No.: 14/902,653

(22) PCT Filed: Jul. 1, 2014

(86) PCT No.: PCT/EP2014/063921
§ 371 (c)(1),
(2) Date: Jan. 4, 2016

(87) PCT Pub. No.: WO2015/003955
PCT Pub. Date: Jan. 15, 2015

(65) Prior Publication Data
US 2016/0170486 A1    Jun. 16, 2016

(30) Foreign Application Priority Data
Jul. 9, 2013 (EP) ..................................... 13446504

(51) Int. Cl.
*G06F 3/01* (2006.01)
*A61B 3/113* (2006.01)
(Continued)

(52) U.S. Cl.
CPC .............. *G06F 3/013* (2013.01); *A61B 3/113* (2013.01); *G06K 9/00604* (2013.01)

(58) Field of Classification Search
CPC ...... G06F 3/013; A61B 3/113; G06K 9/00604
(Continued)

(56) References Cited

U.S. PATENT DOCUMENTS

2003/0098954 A1    5/2003    Amir et al.
2007/0279590 A1    12/2007    Ebisawa
(Continued)

FOREIGN PATENT DOCUMENTS

| EP | 1391176 A1 | 2/2004 |
| EP | 2604180 A1 | 6/2013 |
| WO | WO2013/066334 | 5/2013 |

OTHER PUBLICATIONS

Extended European Search Report issued in European Application No. 13446504.6, dated Dec. 3, 2013, which the instant application claims priority to; 7 pgs.
(Continued)

*Primary Examiner* — Hee-Yong Kim
(74) *Attorney, Agent, or Firm* — Harness, Dickey & Pierce, P.L.C.

(57) ABSTRACT

A device for acquiring a combined eye gaze image of an object under dark-eye effect conditions, with a first camera, a second camera, a first light source and a second light source being located on opposite sides of, and on essentially equal distance to a central optical axis. A control unit is arranged to acquire the combined eye gaze image by capturing, in a first point in time, a first frame of the object with the first camera with the second light source activated, and, at a second point in time, capturing a second frame of the object with the second camera with the first light source activated. The device comprises no additional light sources further away from the central optical axis than the first location and the second location. The device is thereby designed as compact as possible while a sufficient eye gaze tracking accuracy and robustness is maintained.

15 Claims, 3 Drawing Sheets

(51) Int. Cl.
*G06K 9/00* (2006.01)
*H04N 9/68* (2006.01)
*H04N 5/222* (2006.01)

(58) Field of Classification Search
USPC .......................................................... 348/78
See application file for complete search history.

(56) References Cited

U.S. PATENT DOCUMENTS

2010/0157100 A1* 6/2010 Roquemore, III ... H04N 5/2256
348/234
2013/0107214 A1 5/2013 Blixt et al.

OTHER PUBLICATIONS

PCT International Search Report and Written Opinion issued in PCT Application No. PCT/EP2014/063921, dated Sep. 10, 2014, which the instant application claims priority to; 11 pgs.

* cited by examiner

EYE GAZE IMAGING

CROSS-REFERENCE TO RELATED APPLICATIONS

This patent application is a U.S. national stage filing under 35 U.S.C. § 371 of PCT International Application No. PCT/2014/063921 filed Jul. 1, 2014 (published as WO 2015/003955 on Jan. 15, 2015), which claims priority of European application No. 13446504.6 filed Jul. 9, 2013 (published as EP2823751). The disclosures of the applications identified in this paragraph are incorporated herein by reference in their entirety.

FIELD OF THE INVENTION

The present invention relates to a device for illuminating, imaging and detecting the eye, for example relative position of eyelids, the position of the eyes and the gaze direction.

BACKGROUND OF THE INVENTION

For several applications in for example the technical fields of driver analysis in vehicles and user control of personal computers there is a need to acquire information on the users' eye gaze direction, the movements of the eyes and the eyelids and the position of the user. Among possible methods to image and analyze the users eyes there is a group of methods based on detecting reflections on the cornea. Knowledge of the interrelationship between the imaging system and the light source that is reflected in the pupil enables calculation of the eye gaze direction. Using only one camera, it is sometime difficult to correctly determine the eye gaze. This may be solved by using two or more light sources, movable light sources or more than one camera. Using two cameras, a more accurate position and direction of the object's eyes may be calculated, compared to a single camera device.

When the light source is close to the optical axis of the imaging system there will be an internal reflection in the eye which appears brighter than the surrounding, this is called bright eye effect. If the light source is sufficiently removed from the optical axis, the light source will illuminate the eye and the surrounding area without causing an internal reflection, referred to as dark eye effect. A pupil in bright-eye condition may be easier to detect in contrast to its surroundings, but there may be advantages to determine the reflections from the light source on a pupil in dark-eye effect conditions.

In order to acquire a satisfactory dark-pupil image, the light source (flash) should be separated from the camera in the order of 10 degrees from the perspective of the user. In a case where two cameras are used (stereo imaging) the two cameras should also be separated by about 7-10 degrees. For example, in a use case where a person is sitting some 60 centimeters from the eye tracker, the complete imaging device will have two cameras and two light sources arranged over a width of roughly 30 cm. Such a device becomes relatively bulky, and is difficult to implement in a space restricted environment, such as an automobile.

Current eye gaze tracking systems are often adapted for research and development or prototype use. It is therefore desired to develop a device which may be more suitable for mass market use in for example automotive applications or personal computers. Simultaneously it is important that a high functional detection rate and accuracy is maintained so that user acceptance is not lost.

GENERAL DISCLOSURE OF THE INVENTION

It is an object of the present invention to address the shortcomings of the prior art, and to provide an eye gaze tracking device which is as compact as possible. Another object of the invention is to maintain a sufficient eye gaze tracking accuracy and robustness.

According to a first aspect of the invention, these and other objects are achieved with a device according to claim 1, and with a method according to claim 9.

The invention is based on the realization that a satisfactory eye gaze image may be acquired by a first frame and a second frame separated in time, as long as the separation in time is short compared to the normal rate of motion of the object. By separating the activation of the cameras in time, a first and a second light source may be used alternatingly, allowing a sufficient distance between a camera and a light source used to illuminate the object.

Furthermore it is advantageous to have each camera activated together with the light source arranged at the other camera, as this allows for dark-eye effect conditions without expanding the device from the location of the cameras. Consequently the device is kept as compact as possible.

In order to minimize the risk of detrimental effect on the eye gaze tracking due to object movements between each frame of the combined eye gaze image, the frames are preferably taken at a minimal interval without obtaining bright-eye effect conditions.

The expression "light source" is here to be understood as any controllable source of light. For example it may be possible to use any kind of light emitting diode, organic light emitting diode, photo flash, light bulb etc. Each light source may advantageously emit light in a wavelength which is not detectable by the human eye, e.g. infrared, so that the object is not inconvenienced by the device, in which case each camera is preferably also adapted to only capture light of this wavelength or a limited wavelength range comprising this wavelength. Furthermore it should be understood in the context of the invention that each light source may comprise a plurality of light sources arranged to be activated simultaneously at a single activation signal.

According to the invention, there are no additional light sources arranged outside the first and second locations with respect to the optical axis. The extension of the device in a direction normal to the central optical axis is thereby determined by the first and second locations.

A device according to the invention may advantageously be used to detect the direction of gaze of a user. Thus, the "object" that the device is recording is typically at least a part of a head, advantageously the face and at least one of the eyes. The object may be referred to as the "user" even if it may be possible that a second person is utilizing the device on the object or if the device is autonomously capturing combined eye gaze images to provide to an external system or to provide signals representative of the objects' eye gaze.

The device may advantageously be designed based on the application in question, so that the locations are arranged at a distance from each other being sufficient to provide image frames of the object with dark-eye effect conditions, while maintaining the device compact and tracking accuracy as high as possible. Additionally the distance may be selected to minimize the risk of surrounding facial features obstructing the view of one or both eyes of the object.

The expression "location" is here used broadly, to indicate that a camera and a light source arranged in such a location are too close to provide a satisfactory dark-eye image. A distance between a camera and a light source in the same locations thus much smaller than the distance between the locations, typically at least an order of magnitude smaller.

According to one embodiment of the present invention, the separation between the first and second locations is such that an angle formed between two lines between the object and each camera, respectively, is in the range 4-9 degrees. The distance between the object and the device is commonly in the range 40-120 cm. In a typical application, where the object (e.g. face of a user) is approximately on arms length from the device, the separation is in the range of 4-9 cm between the camera and light source used to illuminate the object when this camera is used to acquire a frame.

The time between the first and second points in time is preferably as short as possible, and ideally no longer than the time required for one camera to acquire a frame. As an example, this required time may be 100-500 µs.

In one exemplary embodiment the first camera has a first optical axis and the second camera has a second optical axis, and the first and second optical axis extend in a plane spanned by the central optical axis and a line between the first and second locations. The first and second optical axis may be non-parallel, and typically converge slightly.

The light sources may also preferably be directed to converge onto the optical axis.

According to one embodiment the control unit is arranged to acquire multiple combined eye gaze images by periodically in sequence capturing frames using the first and second camera. The device will thus acquire a video stream of the object.

The cameras will typically have a measurable activation delay, i.e. a delay between an activation pulse and the moment when acquisition of a frame is actually initiated. The control unit is preferably adapted to adapt the activation of the cameras taking such a delay into account, thereby minimizing the time distance between the first and second points in time.

Further, a light source may have measurable illumination delay between activation of the light source and illumination of the object, and a measurable black-out delay between deactivation of the light source and de-illumination of the object. The control unit is preferably adapted to adapt the activation of the cameras taking such delays into account, thereby minimizing the time distance between the first and second points in time.

The principle of combining a first frame and a second frame with a device according to claim 1, and with a method according to claim 9 may be extrapolated to a device comprising further cameras and/or light sources. A third frame is accordingly taken using a third camera and a light source which is separated from the third camera so that it does not cause bright eye effect conditions. The third frame is captured at a third point in time which is preferably no later after the second point in time than the time between the first and second points in time.

The control unit is advantageously adapted so that each combined eye gaze image can be provided at a predetermined image rate. A non-activation pause is introduced by the control unit so that the time between the first frame of each combined eye gaze image corresponds to the predetermined image rate.

The predetermined image rate is typically in the range of 25-1000 Hz.

In the context of the invention a "non-activation pause" refers to that the control unit does not send any activation signals to any camera or light source.

BRIEF DESCRIPTION OF THE DRAWINGS

The present invention will be described in more detail with reference to the appended drawings, showing currently preferred embodiments of the invention.

DETAILED DESCRIPTION OF PREFERRED EMBODIMENTS

Figure 1:
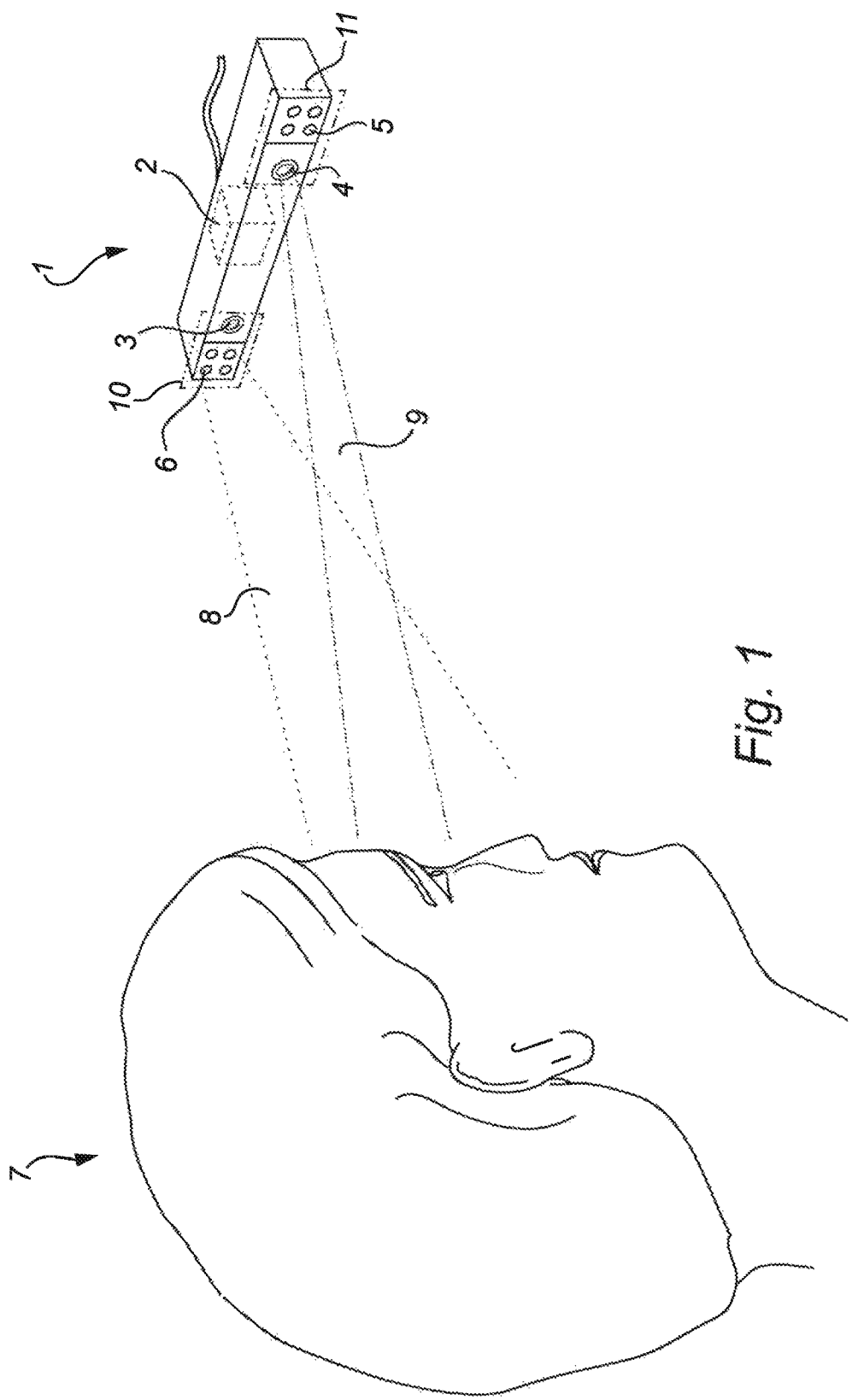
FIG. 1 is a perspective view of a device according to one example embodiment, and an object

FIG. 1 shows a device 1 for acquiring a combined eye gaze image of an object 7 according to an embodiment of the present invention. The device is especially adapted for detection and analysis of eye gaze in dark-eye effect conditions. A device according to the invention may be implemented in many types of applications, such as integrated in a vehicle dashboard or at the screen of a personal computer. However, in the illustrated case the device 1 is shown directed at an object 7 without an application context. The device 1 comprises a control unit 2, a first camera 3, a second camera 4, a first light source 6 and a second light source 5. The first camera 3 and the second camera 4 are preferably electronic image sensor cameras, either of snapshot type or delivering a stream of consecutive images. The images can be in a digital format, e.g. a bitmap format, or in analog form which then can be converted to a digital format, e.g. using a framegrabber circuit (not shown). In the illustrated example each of the first light source 6 and the second light source 5 comprises four light emitting diodes (LEDs). The electromagnetic waves emitted by the LEDs can be of different types, including IR radiation. In some cases it is preferred that the waves are within a relatively narrow wave length range outside the range of visible light, and that each camera is provided with a band pass filter (not shown) corresponding to this range. The influence from the surrounding light is thereby further reduced, as many light sources (computer screens, fluorescent lamps, etc) practically only emit waves in the visible light range. The influence from other sources, e.g. the sun, can be reduced if the total radiated energy in the wave band from the wave emitter is at least a significant fraction of the total sun radiation in the same band. In conventional arrangements with illumination of an object, quite large light sources are used, in order to accomplish active radiation with high intensity evenly distributed over the object. In the device according to the invention, however, each light source preferably has as small aperture as possible, as this is distinguishable from illumination from another source. In conventional arrangements where LEDs are employed for illuminating an object with IR-radiation, normally more than 20 LEDs may be arranged in a rectangular pattern. In one embodiment, it may be sufficient with fewer LEDs in each light source. The number of LEDs can range from one to 19. In order to achieve a satisfying result, it is important that reflexes arising from illumination from the active light source are distinguishable by the image capturing device. Apart from the preferably small light source discussed above, the quality of the combined eye gaze image is dependent upon the ability of the camera to capture high intensity "point" sources of radiation.

Returning to FIG. 1 the device 1 in the illustrated example is a rectangular box with a primary extension in the horizontal direction. The device 1 is arranged at a distance of about 0.5-1 m to the object 7. Relative the object 7 there is a first location 10 leftmost on the device 1, comprising the first camera 3 and the first light source 6. Still relative the object 7 there is a second location 11 rightmost on the device 1, comprising the second camera 4 and the second light source 5. The first location 10 and the second location 11 are spaced apart a distance of 6-8 cm. This separating distance is enough to ensure that a light source active in one location will not result in a bright-eye effect for a camera in the other location, capturing an image frame of the object 7.

The device 1 further comprises a control unit 2 to alternately illuminate 8 the object 7 with a light source in one location while capturing an image frame 9 with a camera in the other location. In the illustrated example the control unit 2 activates the first light source 6 so that it emits light 8 (or IR radiation) at the object 7. Meanwhile the control unit 2 activates the second camera 4 to capture an image frame in its field of view 9.

Figure 2:
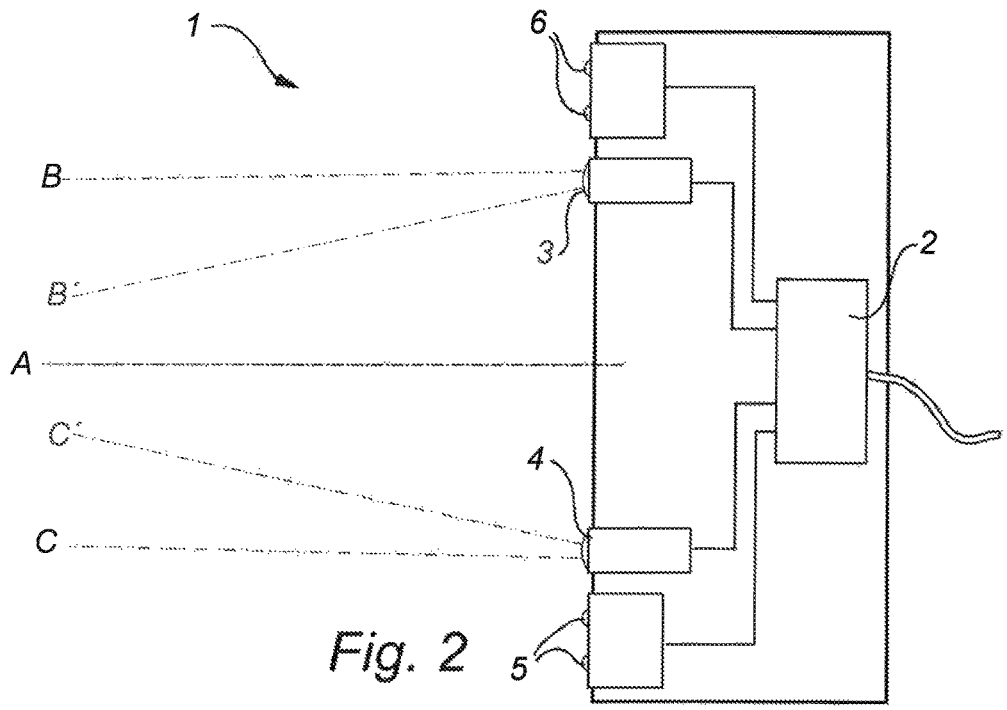
FIG. 2 is a cross section of a device according to one example embodiment

Referring to FIG. 2 the control unit 2 is connected to the first camera 3, the second camera 4, the first light source 6, and the second light source 5 to provide each with activation signals and to receive image frames from the first camera 3 and the second camera 4. The activation signals to the light sources can be provided by alternatingly turning the first 6 and the second 5 light sources on and off. Similarly the control unit 2 alternatingly sends an activation signal to each camera during which the active camera is capturing an image frame. In the illustrated example the control unit 2 is arranged to first activate the first camera 3 together with the second light source 5 to capture a first image frame. Subsequently the control unit will activate the second camera 4 together with the first light source 6 to capture a second image frame. The control unit 2, which has received each frame from the respective camera, can combine the information from each frame to provide a combined eye gaze image. The combined eye gaze image can be provided to an external unit (not shown) or alternatively be used in the control unit 2 to e.g. determine position, direction, etc. of the object's eyes.

Returning to FIG. 2 the device 1 can be said to have a central optical axis A which represents the optical axis of the provided combined eye gaze image. The first camera 3 has an optical axis B and the second camera 4 has an optical axis C, both optical axis B and optical axis C are in the illustrated example essentially parallel to each other in the horizontal plane as seen from the object in FIG. 1. Preferably optical axes B and C converge slightly towards the central optical axis A, as shown in an exaggerated manner with axes C' and B'. This may improve the possibility to triangulate in the combined eye gaze image.

Figure 3:
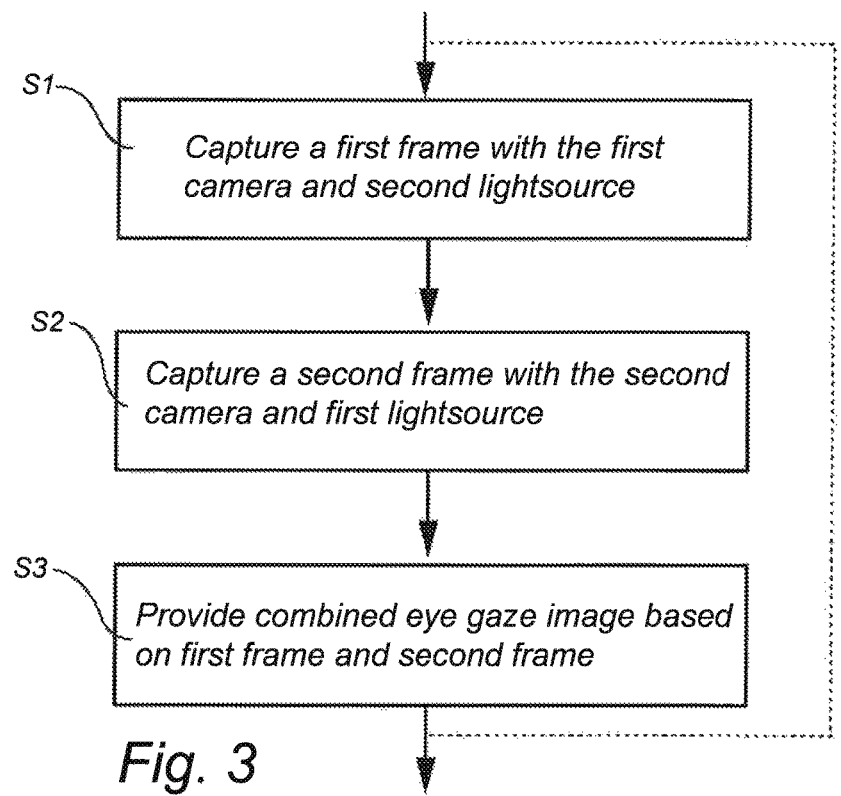
FIG. 3 is a flow chart showing a control of the device according to one example embodiment

Now referring to FIG. 3 where a flow chart showing a control scheme of the device according to one exemplary embodiment of the invention is shown. First, in step S1 a first frame is captured using the first camera and the second light source. Then, in step S2 a second frame is captured using the second camera and the first light source. Further, in step S3 an eye gaze image is provided as a combination of the information comprised in the first frame and in the second frame. Accordingly, the combined eye gaze image may comprise all information from the first frame and the second frame or the combined eye gaze image may comprise a smaller amount of selected or predetermined information from the first and the second frame. The smaller amount of selected or predetermined information is contains e.g. a black and white colorscale (i.e. greyscale), or just a predetermined wavelength spectrum.

Figure 4A:
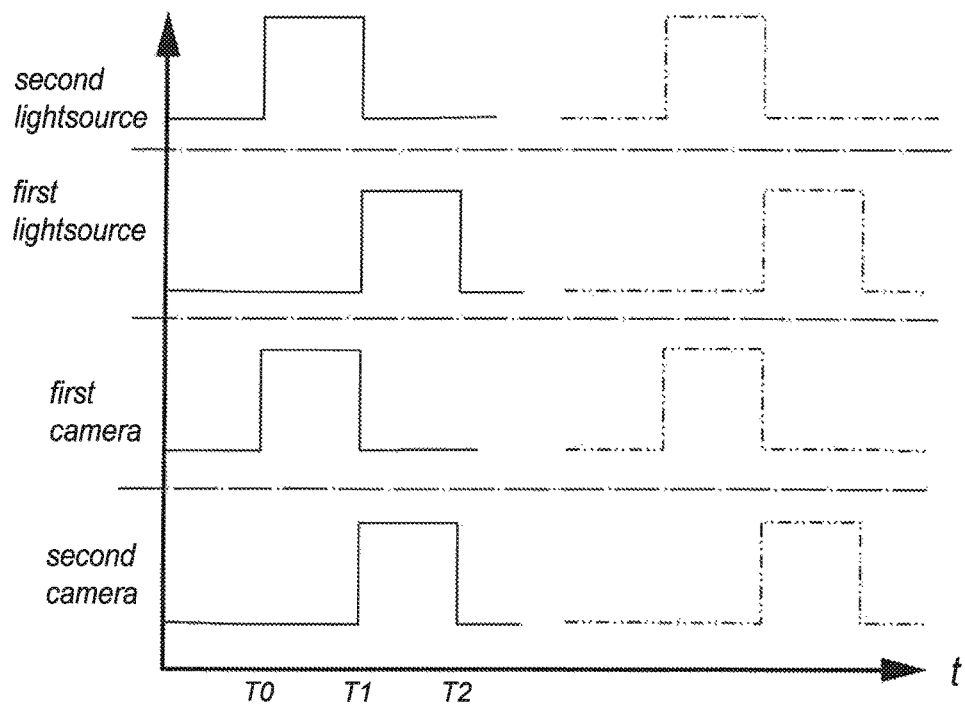
FIG. 4a is a timing graph showing a control of the device according to one example embodiment

In FIG. 4A a graph of the activation signals sent by the control unit 2 to each component of the system according to the method versus time is shown, at a time T0 the second light source 5 and the first camera 3 are activated whereby the first camera 3 captures a first frame at dark-eye conditions. Then, at a first transitional time T1 the second light source 5 and the first camera 3 is deactivated by the control unit 2, and the control unit 2 concurrently activates the first light source 6 and the second camera 4 to capture a second frame at dark-eye conditions. Further, at the second transitional time T2 the first light source 6 and the second camera 4 is deactivated. This process may then be repeated as long as a user or objects needs to be tracked, whereby e.g. an eye gaze may be tracked and the system provides a combined eye gaze image based on the first frame and the second frame comprising this information. In the case of continuous recording, as in repeating the process, it may be advantageous to provide an image rate other than the image rate resulting from capturing a new first frame directly subsequent to the second frame, wherein the image rate would result from the time between T0 and T2. The control unit may advantageously be adapted to introduce a pause after time T2 until the process is repeated, so that a predetermined image rate can be provided for each periodic cycle of time T0.

Figure 4B:
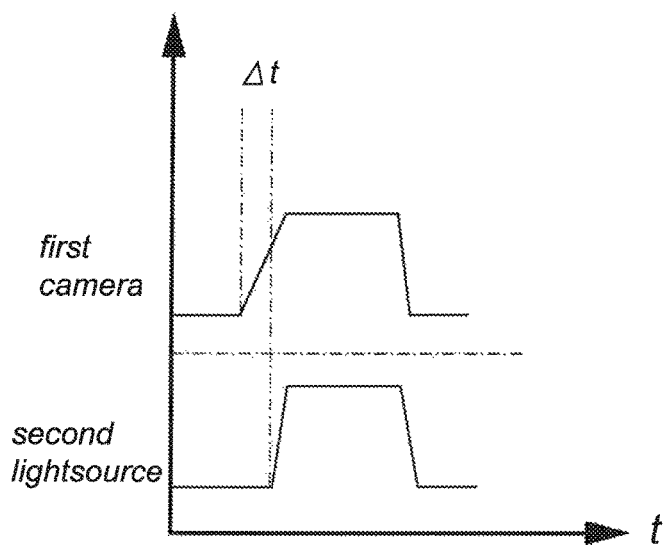
FIG. 4b is a timing graph showing a control of the device according to another example embodiment

In FIG. 4B a transitional time period the second light source and first camera is shown in detail for a device according to one exemplary embodiment of the invention. Note that there is an activation offset Δt for the first camera, wherein the first camera is activated before the second light source. Due to the delay between the activation signal sent from the control unit 2 to the moment when the first camera 3 actually initiates acquisition of a frame the control unit is adapted to take such a delay into account to minimize the delay at any transitional time between two frames. Similarly the first 6 and second 5 light source may have illumination- and black-out delays that are both due to physical characteristics of a light source, when power is provided full illumination i.e. for a LED emittance of the maximum number of photons is not reached until a short time after activation of the LED.

By measuring the illumination delay, black-out delay and activation delay it is possible for the control unit to adapt with activation offsets to generally minimize timing difference in image frames of a combined eye gaze image, thus minimizing any error caused by movements of the object 7 between frames. For example an activation offset is introduced for the second camera as shown in FIG. 4B in such a manner that the first camera may be initiated even during the preceding frame so that it is prepared and ready to capture the first frame when full illumination is provided by the second light source 5. Furthermore, it is noted that the first light source should be non-emitting.

The person skilled in the art realizes that the present invention by no means is limited to the preferred embodiments described above. On the contrary, many modifications and variations are possible within the scope of the appended claims. For example it may be possible to consider that while some cameras have global shutters, meaning that the complete image from the field of view is captured during activation, there are also cameras with rolling shutters. A rolling shutter means that one horizontal line at a time is captured, this opens the possibility of using previous frames to gather information on position of the cornea of the object 7, in terms of specific horizontal lines. With this knowledge it may be possible to further minimize the time between frames by illuminating only during capture of a cornea. This way it may even be possible to slightly overlap frames, as long as bright-eye effect conditions are not present for each respective camera.

The invention claimed is:

1. A device for acquiring a combined eye gaze image of an object, said device having a central optical axis directed at the object, said device comprising:
   a first camera, a second camera, a first light source, and a second light source, said first camera and said first light source are arranged in a first location too close to each other to provide a satisfactory dark-eye image, said second camera and said second light source are arranged at a second location too close to each other to provide a satisfactory dark-eye image, said first and second locations being located on opposite sides of, and an essentially equal distance to, said central optical axis; and
   a control unit for controlling said first and second cameras and said first and second light sources;
   wherein:
      said device comprises no additional light sources farther away from said central optical axis than said first location and said second location; and
      said control unit is arranged to acquire said combined eye gaze image by capturing, in a first point in time, a first frame of said object with said first camera with said second light source activated, and, at a second point in time, capturing a second frame of said object with said second camera with said first light source activated.

2. The device according to claim 1, wherein a distance between said first location and said second location is within a range from 4 centimeters to 9 centimeters.

3. The device according to claim 1, wherein said first and second points in time are separated by 100 to 500 μs.

4. The device according to claim 1, wherein:
   said first camera has a first optical axis;
   said second camera has a second optical axis; and
   said first optical axis and said second optical axis extend in a plane spanned by said central optical axis and an axis normal to a line between said first location and said second location.

5. The device according to claim 4, wherein said first and second optical axis are non-parallel.

6. The device according to claim 1, wherein said control unit is arranged to acquire multiple combined eye gaze images by sequentially capturing frames using said first and second camera.

7. The device according to claim 1, wherein:
   said first light source and said second light source each have a measurable illumination delay and a measurable black-out delay; and
   said control unit is adapted to adapt activation of each camera in relation to activation of each light source taking said illumination delay and said black-out delay into account.

8. The device according to claim 1, wherein:
   said first camera and said second camera each have a measurable activation delay; and
   said control unit is adapted to adapt activation of each camera taking such a delay into account, thereby minimizing the time distance between the first and second points in time.

9. The device according to claim 1, wherein a distance between the first camera and the first light source, and a distance between the second camera and the second light source, are both at least an order of magnitude smaller than a distance between the first and the second locations.

10. A method for acquiring a combined eye gaze image of an object with a device including a central optical axis, a first camera, a second camera, a first light source, and a second light source, said method comprising the steps of:
   providing the first camera and the first light source in a first location too close to each other to provide a satisfactory dark-eye image;
   providing the second camera and the second light source in a second location too close to each other to provide a satisfactory dark-eye image, said first and second locations being located on opposite sides of, and an essentially equal distance to, said central optical axis directed at the object;
   capturing, in a first point in time, a first frame of said object using said first camera with said second light source activated;
   capturing in a second point in time, a second frame of said object using said second camera with said first light source activated; and
   combining said first and second frames to form said combined eye gaze image; wherein the device comprises no additional light sources farther away from said central optical axis than said first location and said second location.

11. The method according to claim 10, wherein said steps of capturing a first and second frame of said object further comprises activating said first and second light source at a time offset, relative activation of said first and second camera, respectively.

12. The method according to claim 10, wherein said steps of capturing a first and second frame of said object further comprises deactivating said first and second light source at a time offset, relative activation of said first and second camera, respectively.

13. The method according to claim 10, wherein said step of capturing a second frame of said object further comprises activating said first light source at an activation offset relative activation of said second camera.

14. The method according to claim 10, wherein said step of capturing a second frame of said object further comprises activating said second light source at an activation offset relative activation of said second camera.

15. The method according to claim 10, wherein a distance between the first camera and the first light source, and a distance between the second camera and the second light source, are both at least an order of magnitude smaller than a distance between the first and the second locations.

* * * * *